United States Patent [19]

Lacks et al.

[11] Patent Number: 5,002,875

[45] Date of Patent: Mar. 26, 1991

[54] **PLASIMIDS CONTAINING THE GENE FOR DNA POLYMERASE I FROM *STREPTOCOCCUS PNEUMONIAE***

[75] Inventors: Sanford A. Lacks, Brookhaven; Susana Martinez, Sound Beach, both of N.Y.; Paloma Lopez; Manuel Espinosa, both of Madrid, Spain

[73] Assignee: The United States of America as represented by the United States Department of Energy, Washington, D.C.

[21] Appl. No.: 90,623

[22] Filed: Aug. 28, 1987

[51] Int. Cl.$^5$ .................... C12N 15/52; C12N 15/63; C12N 15/00

[52] U.S. Cl. ................... 435/69.1; 435/172.3; 435/320.1; 435/196; 536/27; 935/60

[58] Field of Search .................... 536/27; 935/14, 60, 935/82; 435/320, 199, 69.1, 172.3

[56] References Cited

U.S. PATENT DOCUMENTS

| | | | |
|---|---|---|---|
| 4,371,625 | 2/1983 | Tiollais | 435/317 |
| 4,374,927 | 2/1983 | Sninsky et al. | 435/68 |
| 4,460,688 | 7/1984 | Sanders et al. | 435/172.3 |
| 4,506,013 | 3/1985 | Hershberger et al. | 435/172.3 |
| 4,579,821 | 4/1986 | Palmiter et al. | 435/172.3 |

OTHER PUBLICATIONS

Lacks, "Mutants of *Diploc pneu.* that lack DNases & Other Activities Possibly Pertinent to Genet Transformation", J. Bact. 101:373-383 (1970).
Johnston, L. H., The Use of a Novel Plate Assay in a Search for Yeast Mutants Defective in DNases MGG, 152: 219-22, 1977.
Rosenthal & Lacks, Nuclease Detection in SDS-P&GE, Anal. Biochem 80(1): 76-90, 1977.
Major, P. et al., Use of Et-Br-DNA Agar Plates for the Detection of Staph Produced Heat-Stable DNases, Kiserl. Orvostad. 34: 313 (1982).
Stassi et al., *PNAS, U.S.A.,* 78, 7028-7032 (1981).
Lopez et al., *Mol. Gen. Genet.,* 195, 402-410 (1984).
Minkley et al., *J. Biol. Chem.,* 259, 10386-10392 (1984).
Mejean et al., *J. Bacteriol.,* Jun. 1984, 1175-1178.
Balganesh et al., *Gene,* 29, 221-230 (1984).

*Primary Examiner*—Richard A. Schwartz
*Assistant Examiner*—S. L. Nolan
*Attorney, Agent, or Firm*—Margaret C. Bogosian; James W. Weinberger; William R. Moser

[57] ABSTRACT

A method is disclosed for cloning the gene which encodes a DNA polymerase-exonuclease of *Streptococcus pneumoniae*. Plasmid pSM22, the vector containing the pneumocccal polA gene, facilitates the expression of 50-fold greater amounts of the PolI enzyme.

3 Claims, 1 Drawing Sheet

PLASMIDS CONTAINING THE GENE FOR DNA POLYMERASE I FROM *STREPTOCOCCUS PNEUMONIAE*

The U.S. Government has rights in this invention pursuant to Contract Number DE-AC02-76CH00016, between the U.S. Department of Energy and Associated Universities Inc.

STATEMENT OF DEPOSIT

The plasmids of the present invention have been deposited in the American Type Culture Collection, in Rockville, Md., under conditions which assure maintenance of the deposits in accordance with the rules established under M.P.E.P. 608.01(p). Plasmid pSM22 may be obtained under ATCC No. 67496; pLS1 under ATCC No. 67497; and pSM23 under ATCC No. 67498.

BACKGROUND OF THE INVENTION

The present invention discloses a procedure for cloning the gene encoding a DNA polymerase-exonuclease of *Streptococcus pneumoniae*. In its broader application, the present invention discloses a procedure for cloning and characterizing genes that encode proteins with nuclease activity in the *Streptococcus pneumoniae* host/vector system. As used in this invention, nuclease is an enzyme capable of hydrolizing internucleotide linkages of a nucleic acid. Exonuclease is an enzyme that hydrolyzes only a terminal phosphodiester bond of a nucleic acid. DNA polymerase is an enzyme catalyzing a template-dependent synthesis of DNA from its deoxyribonucleoside 5'-triphosphate precursors.

Bacteria generally contain several different DNA polymerase enzymes. In the best characterized case— gram-negative *Escherichia coli*—three enzymes are found: PolI, which is present in the highest molar concentration, and has been implicated in DNA repair; PolII, for which no function is known; and PolIII, which is responsible for chromosomal DNA synthesis. All three enzymes exhibit 3' to 5' exonuclease activity, and PolI and PolIII also exhibit 5' to 3' exonuclease activity [extensively reviewed in Kornberg, A., *DNA Replication*, W. H. Freeman and Co., San Francisco (1980) and Minkley et al., *J. Biol. Chem.*, 259:10386–10392 (1984)].

Three DNA polymerases were also found in gram-positive *Bacillus subtilis*. Like *E. coli*, the PolI polymerase of *B. subtilis* is the predominant enzyme (and implicated in DNA repair), and PolIII functions in chromosomal replication. PolIII exhibits exonuclease activity, but only in the 3' to 5' direction. PolII does not show exonuclease activity, and the exonuclease activity of PolI has not been clarified yet.

On the other hand, the predominant polymerase in gram-positive *Streptococcus pneumoniae* exhibits exonuclease activity after only partial purification [Lacks, S., *J. Bacteriol.*, 101:373-383 (1970)]. Cloning of the gene for this polymerase, PolA, was accomplished by an approach that depended upon the exonuclease activity of the enzyme, a procedure far different from that used for cloning the *E. coli* gene [Kelley et al., *PNAS, U.S.A.*, 74:5632-5636 (1977)]. As detailed below, the pneumococcal gene is cloned in a gram-positive cloning system using a broad host-range multicopy plasmid vector [based on a procedure disclosed in Stassi et al., *PNAS, U.S.A.*, 78:7028-7032 (1981)]. Unique features of the approach include the screening of clones for exonuclease activity by a DNase colony assay, and the characterization of the product of the cloned gene by a method for detecting nuclease activity in polycrylamide gels after electrophoresis and in the presence of SDS. Previously these techniques have been used for the study and characterization of proteins with nuclease activity, but never for detecting DNA polymerases. As most of the known DNA polymerases show exonuclease activity, this procedure can be generally applicable to the cloning of genes that codify for DNA polymerases, and this method is more rapid and convenient than the one used for the cloning of the *E. coli* polA gene.

SPECIFIC DESCRIPTION OF THE INVENTION

Figure 1:
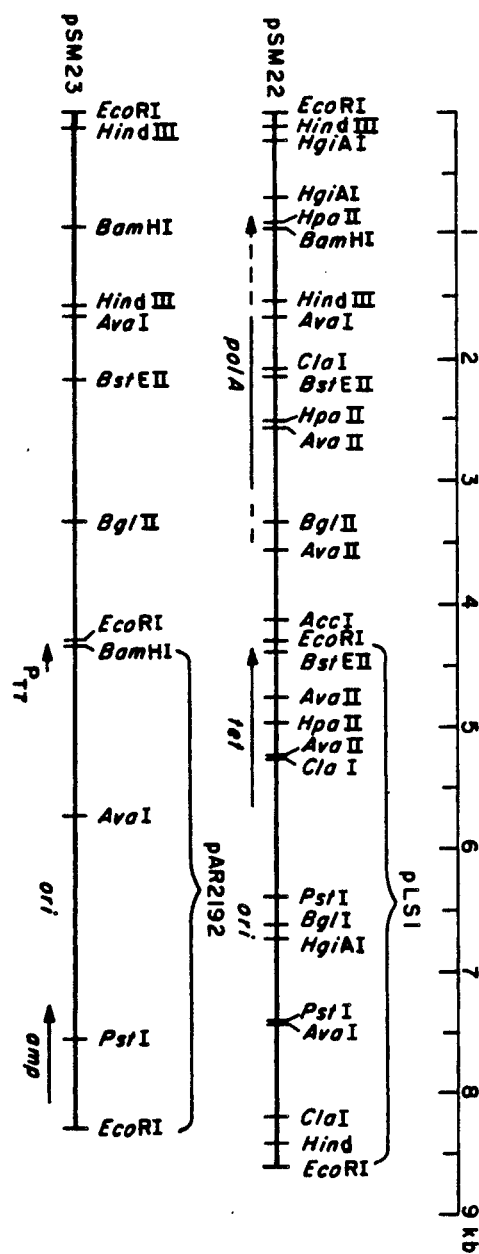
FIG. 1 contains the restriction maps of recombinant plasmids pSM22 and pSM23. The genetic symbols used are: PolA, encodes PolI of *S. pneumoniae*; tet, encodes the protein responsible for tetracycline resistance; ori, is the presumed origin of replication in the vectors; amp, encodes beta-lactamase; $P_{T7}$, is the promoter for transcription by phage T7 RNA polymerase. The arrows indicate the direction of transcription. In pSM24 the chromosomal fragment (heavy line) is reversed relative to its position in pSM23.

A restriction map of the recombinant plasmids of the present invention is shown in FIG. 1. Deletions were introduced into the plasmid by removing restriction fragments and religation, according to methodologies well known to practitioners in the art. These deletion experiments show that both the 3.2-kb HindIII-fragment (extending into the left side of the chromosomal insert) and the 3.3-kb BstEII fragment (extending into the right side of the chromosomal insert) were essential for gene function. No increase of nuclease activity over the host-cell background is observed in these deletion plasmids. From the nuclease detection gels (described in the Examples), the pneumococcal PolI has a mass of about 100 kDa, requiring a coding capacity of about 2.7 kb (or about 63% of the 4.3-kb chromosomal insert).

Plasmid pSM22 is a recombinant plasmid containing a segment of chromosomal DNA from *S. pneumoniae* inserted into plasmid pLS1. It is constructed by cleaving chromosomal DNA from *S. pneumoniae* strain R6 with restriction enzyme EcoRI. 5 ug of these EcoRI-cut DNA fragments are ligated with 1 ug of EcoRI-cut pLS1.

Similarly, recombinant plasmids pSM23 and pSM24 are constructed by inserting the chromosomal DNA segment of pSM22 into plasmid pAR2192 (in opposite orientations, thus obtaining each recombinant plasmid). Briefly, 1 ug each of pSM22 cut with EcoRI and PstI and of pAR2192 cut with EcoRI are ligated. The restriction maps of these plasmids are also shown in FIG. 1.

Bacterial cultures were grown and transformed with the above-noted plasmids using the well known techniques described in Lopez et al., *Mol. Gen. Genet.*, 195:402–410 (1984). Although the invention is not intended to be limited by the particular bacterial strain(s) noted, the following strains are representative of the invention: *Streptococcus pneumoniae* strain R6 (nonencapsulated, nonpathogenic, and "wild-type") and R6 derivatives—577 (end-14), 593 (end-1), 641 (end-1 noz-19 exo-2), 642 (exo-5), and 708 (end-1 exo-2 trt-1 hex-4 malM594). The end and noz (for no zone) mutations affect the gene encoding the major endonuclease of *S.*

*pneumoniae*, and the exo mutations affect the major exonuclease. The *Bacillus subtilis* strain is CU403, described in Reeve et al., *J. Bacteriol.*, 114:860-873 (1973); the *Escherichia coli* strain is BL21DE3, described in Studier et al., *J. Mol. Biol.*, 189:118-130 (1986).

These bacterial cultures were treated with plasmid DNA at 1.0 ug/ml. Tranformants were selected in agar medium containing tetracycline (Tc) at 1 ug/ml for *S. pneumoniae*, and 50 ug/ml for *B. subtilis;* *E. coli* was selected in agar medium containing ampicillin (Ap) at 50 ug/ml.

As is shown in more detail in the Examples, chromosomal DNA was prepared from *S. pneumoniae* according to the procedures described in Hotchkiss, R. D., *Methods of Enzymol.*, 3:692-696 (1957). Purified plasmids were prepared by the procedure of Currier et al., *Anal. Biochem.*, 76:431-441 (1976). Crude plasmid preparations, called alkaline lysates, were prepared from *E. coli* by the method of Birnboim et al., *DNA Nucl. Acids Res.*, 7:1513-1523 (1979), and from *S. pneumoniae* by a modification of that method, described in Stassi et al., *PNAS, U.S.A.*, 78:7028-7032 (1981). Cleared lysates of *B. subtilis* were prepared as described in Espinosa et al., *Mol. Gen. Genet.*, 188:195-201 (1981).

The use of restriction endonucleases are well known to the practitioners in the art, and are all commercially available. Analytical gel electrophoresis of plasmids and restriction fragments is performed in 1% agarose or 5% polyacrylamide (PA), with staining by ethidium bromide. Ligation protocols are described in Stassi et al., cited above.

EXAMPLE 1

Cloning of a Chromosomal Gene

Cloning was accomplished in an *S. pneumoniae* host with the vector pLS1. Chromosomal DNA of the wild-type strain, R6, was cut with EcoRI and ligated with pLS1 cut at its single EcoRI site. The ligation mixture was used to transform strain 708, a *S. pneumoniae* strain deficient in the major nucleases [and described in Lacks, S., *J. Bacteriol.*, 101:373-383 (1970)]. Tc-resistant transformants were screened by the DNase plate assay (described in Example 2) for the ability of colonies to form colorless zones indicative of elevated nuclease levels in the clone. To increase the proportion of transformant clones (increasing the ratio of recombinant plasmids to reconstituted vector plasmids), the ligation mixture was enriched, in this case, by chromosomal facilitation [Balganesh et al, *Gene*, 29:221-230 (1984)].

Three of the 500 Tc$^R$ colonies showed larger zones, and all three contained plasmids of similar size. One of the plasmids picked from these colonies, plasmid pSM22, contained a 4.3-kb insert of chromosomal DNA.

EXAMPLE 2

Crude extracts of various strains of *S. pneumoniae* or *B. subtilis*, with or without pSM22, were analyzed for nuclease components by a gel DNase assay method disclosed in Rosenthal et al, *Anal. Biochem.*, 80:76-90 (1977). This procedure permits the detection of enzyme activities after SDS-PA gel electrophoresis and the determination of the size of the polypeptide responsible for the activity. Briefly, total cell extracts containing approximately 50 ug of protein were subjected to electrophoresis in the presence of SDS in a PA slab gel containing a linear gradient of 5-15% polyacrylamide, and DNA at 30 ug/ml. The gel DNase assays of extracts from cells with and without pSM22 indicated the presence of the following extracts from strains of *S. pneumoniae*, unless indicated otherwise: 708 (end-1 exo-2); 708 (pSM22); 641 (end-1, noz-19, exo-2); 641 (pSM22); 577 (end-14); 593 (end-1); 642 (exo-5); R6 (pSM22); R6 (wild type); *B. subtilis* CU403 (pSM22); and *B. subtilis* CU403. The gel was incubated for 62 hours before straining. Migration of the marker proteins showed on the left margin [sizes in kDa (kd)] of the assay; positions of the pneumococcal enzymes showed on the right margin. Strians of *S. pneumoniae* that are wild-type for the major endonuclease give a strong nuclease band at 25 kDa. Strains carrying the leaky end-1 mutation give a weak band at this position. This band is very faint in mutants containing noz-19, and is absent in end-14 mutants. Strains containing the wild-type gene for the major exonuclease give a band at 38 kDa. In all strains of *S. pneumoniae* that do not contain plasmid pSM22, a faint nuclease band was observed at 100 kDa. This activity corresponds to the enzyme elicited by the cloned gene, because a much stronger band was seen in this position when the strains carried pSM22. This enzyme is a DNA polymerase-exonclease.

EXAMPLE 3

That plasmid pSM22 contains the structural gene for the polymerase-exonuclease is indicated by expression of the cloned nuclease activity in a foreign host. As shown in Example 2, pSM22 was transformed into *B. subtilis*, and only those host cells containing the recombinant plasmid showed the nuclease band at 100 kDa. The band just below the main endonuclease band is derived from a proteolytic fragment of the endonuclease. Several bands, some diffuse, in the range of 40 to 90 kDa were visible when pSM22 was present. These bands may also derive from proteolytic fragments of the 100 kDa polypeptide that retains nuclease activity.

EXAMPLE 4

Assays of DNA polymerase and nuclease activities in crude extracts of cells that do or do not carry pSM22 show that both activities are increased proportionally (by a factor of approximately 15) in the presence of the plasmid (see the Table, below). This was demonstrated in a strain of *S. pneumoniae* lacking the major endonuclease and exonuclease, in which the residual nuclease activity was predominantly due to the main polymerase-exonuclease of this bacteria. Work on purification of the protein encoded by the cloned gene shows that the protein is produced in ten-fold higher amounts in the presence of the plasmid than without the plasmid. Furthermore, the protein exhibits both 3' and 5' exonuclease activities. The cloned gene therefore encodes an enzyme similar to *E. coli* PolI, and as part of this invention, is designated polA of *S. pneumoniae*.

Cultures of *S. pneumoniae* were grown in CH medium to $A_{650}=0.8$. Cultures of *E. coli* were grown in M9 medium containing 0.2 mg Ap/ml to $A_{600}=0.5$. IPTG was added to 0.5 mM, and incubation was continued for 2 hours to give $A_{600}=1.1$. Cells from 1 liter were sedimented by centrifugation for 10 minutes at $5000 \times g$, washed by suspension in 40 ml of buffer (containing 0.5M NaCl, 3 mM beta-mercaptoethanol, 0.1 mM EDTA, and 10 mM Tris.HCl, pH 7.6), centrifuged again, and suspended in 10 ml of the same buffer. Total cell extracts were prepared by passing the cell suspensions through a French pressure cell and clarifying them by centrifugation for 20 minutes at 20,000×g. Protein content of the extracts (approximately 15 mg/ml) was determined. Exonuclease activity was determined by incubating samples of extract at 30° C. in 40 ul of a mixture containing 10 mM Tris.HCl (pH 7.6), 3 mM beta-mercaptoethanol, 2 mM MnCl$_2$, 16 ug bovine serum albumin, and 0.2 ug [$^3$H]DNA (prepared from strain 470 grown with [$^3$H-methyl]thymidine, and having a specific activity of 22,000 cpm/ug). Exonuclease reactions were terminated by addition of 40 ul of 3.5% perchloric acid; after 20 minutes at 0° C., the mixture was centrifuged and 60 ul of the supernatant fluid was taken for scintillation counting. Pol activity was determined by incubating samples of extract at 30° C. in 0.1 ml of a mixture containing 10 mM Tris.HCl (pH 7.6), 3 mM mercaptoethanol, 5 mM MgCl$_2$, 40 ug bovine serum albumin, 4 ug salmon sperm DNA (previously nicked with pancreatic DNase), 15 uM each of dATP, dGTP, and dCTP, 3 uM TTP, and 20 nCi of [$^3$H]TTP at 55 Ci/mmol. Reactions were terminated by chilling, and the assay mixtures were applied to DEAE-paper disks, which were then washed six times with 0.5M Na$_2$HPO$_4$, twice with water, and once with ethanol, and dried. Tritium remaining on the disk was counted with an efficiency of 55% in a liquid scintillation system. Units correspond to nucleotides released or incorporated in nmol/h at 30° C.

THE TABLE

DNA polymerase and exonuclease activity in total cell extracts

| Bacterial strain | Specific enzyme activity (units/mg protein) | |
| --- | --- | --- |
|  | Exonuclease | Polymerase |
| S. pneumoniae 641 | 5 | 12 |
| S. pneumoniae 641 [pSM22] | 44 | 218 |
| E. coli BL21DE3[pAR2192] | 16 | 8 |
| E. coli BL21DE3[pSM23] | 212 | 1127 |

EXAMPLE 5

To obtain the hyperexpression of the enzyme encoded by the pneumococcal polA gene, a cloned insert of the present invention was introduced into a T7 RNA polymerase promoter expression system, described in Studier et al, J. Mol. Biol., 189:113-130 (1986). One ml cultures of E. coli carrying pSM23 or pSM24 were grown at 37° C. to A$_{600}$=0.5 in M9 medium containing 0.2 mg Ampicillin/ml, 0.5 umols isopropylthiogalactoside (IPTG), and in come cases, 0.2 mg rifampicin. After various periods of incubation, 10 pmol of [$^{35}$S]methionine (1000 Ci/mmol) were added. After five minutes, the reaction was terminated by chilling the culture, centrifuging the cells, suspending the cells in 0.2 ml of sample loading solution (50 mM Tris.HCl, 2 mM EDTA, 1% sodium dodecyl sulfate (SDS), 1% beta-mercaptoethanol, 0.025% bromphenol blue, and 10% glycerol). The mixture was then heated for 3 minutes at 100° C.

Bacteria cell extracts containing indicated amounts of protein were subjected to electrophoresis in the presence of SDS in a slab gel containing a linear gradient of 5-15% PA and DNA at 30 ug/ml. This electrophoresis showed that the polA nuclease was expressed in the presence of pSM23, but not pSM24, indicating that transcription of the gene must proceed in the direction of the BglII site to the BamHI site.

EXAMPLE 6

Synthesis of proteins in E. coli carrying plasmids containing the polA gene of S. pneumoniae.

Cells of E. coli strain BL21DE3 containing either pSM23 or pSM24 were induced with IPTG for various periods ranging from 30 minutes to 180 minutes with or without the addition of rifampicin, an antibiotic which blocks transcription by the cellular RNA polymerase. The cultures were then pulse-labeled with [$^{35}$S]methionine. The main protein produced with pSM24 in the presence of rifampicin is the 29-kDa beta-lactamase product of the amp gene in the vector. With pSM23, a band at 100 kDa that corresponds to the pneumococcal PolI protein is evident in the presence of rifampicin, in addition to the 29-kDa beta-lactamase and its 31-kDa precursor. In the absence of rifampicin, labeled bands corresponding to cellular proteins are evident, but the products under the T7 promoter control stand out. After 2 hours induction with IPTG, the rate of synthesis of such products was maximal. At this time, approximately 25% of the protein being synthesized appear to be products of the cloned pneumococcal polA gene.

We claim:

1. Plasmid pSM22, deposited in the American Type Culture Collection under ATCC No. 67496, which includes the polA gene of Streptococcus Pneumoniae encoding a DNA polymerase in a broad-host-range vector.

2. Plasmid pSM23, deposited in the American Type Culture Collection under ATCC No. 67498, which includes the polA gene of Streptococcus pneumoniae encoding a DNA polymerase in a high-expression vector of Escherichia coli.

3. A process for the production of a DNA polymerase-exonuclease protein comprising:
   (a) generating a genomic library of Streptococcus pneumoniae using a multicopy streptococcal vector;
   (b) transforming bacterial host cells deficient in nucleases;
   (c) screening the transformed cells for exonuclease activity using a DNase colony assay;
   (d) isolating nuclease-positive clones containing the desired recombinant plasmid, producing a DNA polymerase-exonuclease protein; and
   (e) isolating said protein using an assay for detecting nuclease activity.

* * * * *